United States Patent [19]

Schweikert et al.

[11] Patent Number: 4,596,797

[45] Date of Patent: Jun. 24, 1986

[54] USE OF AROMATASE-INHIBITORS FOR PROPHYLAXIS AND/OR TREATMENT OF BENIGN PROSTATIC HYPERPLASIA

[75] Inventors: Hans-Udo Schweikert, Bonn-Roettgen; Ulf Tunn; Theodor Senge, both of Castrup-Rauxel; Friedmund Neumann, Berlin, all of Fed. Rep. of Germany

[73] Assignee: Schering Aktiengesellschaft, Berlin and Bergkamen, Fed. Rep. of Germany

[21] Appl. No.: 733,436

[22] Filed: May 13, 1985

Related U.S. Application Data

[63] Continuation of Ser. No. 448,672, Dec. 10, 1982, abandoned, which is a continuation-in-part of Ser. No. 307,332, Sep. 30, 1981, abandoned, and a continuation-in-part of Ser. No. 307,331, Sep. 30, 1981, abandoned.

[30] Foreign Application Priority Data

May 10, 1982 [GB] United Kingdom ................ 8213404

[51] Int. Cl.$^4$ ............................................. A61K 31/56
[52] U.S. Cl. .................................... 514/177; 514/178; 514/453
[58] Field of Search ................ 424/240; 514/170, 177, 514/178, 453

[56] References Cited

U.S. PATENT DOCUMENTS

| | | | |
|---|---|---|---|
| 3,423,507 | 1/1969 | Neri | 424/243 |
| 4,055,641 | 10/1977 | Benson et al. | 424/243 |
| 4,235,893 | 11/1980 | Brodie et al. | 424/243 |
| 4,310,523 | 1/1982 | Jovanovics et al. | 424/243 |

FOREIGN PATENT DOCUMENTS 0100566 6/1983 European Pat. Off. ............ 424/243

OTHER PUBLICATIONS

Schwarzel et al., "Endocrinology", (1973) vol. 92, No. 3, pp. 866–880.
Robert W. Brueggemeier et al., *Journal of Medicinal Chemistry*, 1978, vol. 21, No. 10, pp. 1007–1011.
Schweikert, Horm. Metab. Res. 11, 635–640 (1979).
Schweikert et al., Excerpta Medica, Ed: Schroeder et al., pp. 126–133 (1980).
Schweikert, Excerpta Medica, Ed: Hamerstein et al., (1979), Amsterdam, Oxford, Princeton.
Weinstein et al., J. Clin. Invest. 53, 1–6 (1974).
McDonald et al., J. Clin. Endocrinol. Metabl. 27, 1103–1111, (1967).
Vigersky et al., J. Clin. Endocrin. and Metabl. 52, pp. 897–902 (1981).
Barone et al., J. Clin. Endocrin. and Metab. 49, 672–676 (1979).
Marynick et al., J. Clin. Endocrin and Metab. 49, 396–398 (1979).
Siiteri et al., J. Ster. Biochem. 6, 317–332 (1975).
Korenman (Geller/Albert), Endocrine Aspects of Aging, Elsevier Science Publishing Co., Inc. (1982), pp. 137–139.
Funk et al., Acta Endocrinologica 1982, 100:462–472.
Grayhack (Franks, Brendler), National Institute of Health, Feb. 20–21, 1975, DHEW Publication No. 76–1113, pp. 63–71, 85, 101–103.
Hinman, Jr., (Tannenbaum, DeKlerk), Springer-Verlag, New York, pp. 64–67, 69, 71–72; 262–268.

*Primary Examiner*—Elbert L. Roberts
*Attorney, Agent, or Firm*—Millen & White

[57] ABSTRACT

Aromatase-inhibitors are used in a method of prophylaxis and/or treatment by therapy of prostatic hyperplasia. Pharmaceutical preparations suitable for such a use comprise an aromatase-inhibitor. A particularly preferred aromatase-inhibitor is, for example, testolactone.

32 Claims, No Drawings

USE OF AROMATASE-INHIBITORS FOR PROPHYLAXIS AND/OR TREATMENT OF BENIGN PROSTATIC HYPERPLASIA

CROSS-REFERENCE TO RELATED APPLICATION

This application is a continuation of U.S. Ser. No. 448,672, filed on Dec. 10, 1982, now abandoned which is a continuation-in-part of U.S. application Ser. No. 307,332 of Sept. 30, 1981 now abandoned and of U.S. application Ser. No. 307,331, of Sept. 30, 1981 now abanonded and is related to U.S. application Ser. No. 448,673 filed on even date, all of these disclosures being entirely incorporated by reference herein.

BACKGROUND OF THE INVENTION

The present invention is concerned with the use of aromatase-inhibitors in the prophylaxis and/or treatment by therapy of benign prostatic hyperplasia (BPH), and with pharmaceutical preparations suitable for such use.

Benign prostatic hyperplasia involves a benign enlargement of the prostate gland which starts in the so-called "inner" prostate gland. Discomfort can be attributed primarily to the obstructions of the urethra that occur. Voiding of the bladder is impeded and residual urine is retained. Without surgical treatment uremia may occur.

Up to now it has been almost impossible to treat this disorder, very frequent in older men, using medicaments. The phyto-preparations used for this purpose, such as, for example, $\beta$-sitosterin, mixtures of various plant extracts and combinations of plant extracts with the neurotropic spasmolysant azoniaspirochloride have proved ineffective in a one year study. Although the patients under therapy experienced an improvement in the micturition symptom, a regression of the hyperplastic prostate gland was not achieved.

Hormones, too, find application in the treatment of prostatic hyperplasia. Of these substances the depot gestagen gestonorone caproate is worthy of special mention. Compared with the phyto-preparations, an improved action is obtained with gestonorone caproate. The prolonged duration of micturition before the treatment is distinctly shortened and the maximum flow value (flow of urine per unit of time) is improved. A distinct reduction in the size of the adenoma cannot, however, be detected in this case either.

Prostatic hyperplasia involves a benign enlargement of the prostate gland, in which both the interstice (stroma) and the epithelium participate to a varying degree. Hormonal effects have been strongly implicated in the etiology. Heretofore, it has been presumed that abnormal levels of androgens contribute to the enlargement. As a result, antiandrogenic therapy has been suggested by many. See, e.g., U.S. Pat. No. 3,423,507 (e.g., administration of the antiandrogen, cyproterone acetate, i.e., 1$\alpha$, 2$\alpha$-methylene-6-chloro-17$\alpha$-acetoxy-6-dehydroprogesterone), U.S. Pat. No. 4,055,641, etc. More recently, evidence has been gathered which suggests that, inter alia, a shifting of the estrogen/androgen ratio in favor of estrogen may be regarded as a cause of BPH. That is, suggestions have been made that an increase in the estrogen level can contibute to the enlargement of the prostate. Thus, the state of the art establishes an expectation that an increase in the estrogen level and/or an increase in the androgen level will contribute toward BPH, while a shifting of the estrogen/androgen ratio in favor of the amount of estrogen, inter alia, may also be regarded as a cause of BPH. Moreover, various investigations have shown that in older men the concentrations of serum testosterone fall off; at the same time the proportion of SHBG (sex hormone binding globulin, specific transport protein for steroids) increases, so that the biological availability of androgens decreases still further.

Thus, the literature establishes an expectation of a benign enlargement of the prostate due to an increase in the estrogen level alone, an increase in the androgen level alone, or an increase in the estrogen/androgen ratio.

For example, in U.S. Pat. No. 4,310,523 it is proposed that a combination of an antiestrogen and an antiandrogen is effective for the prophylaxis and/or therapy of benign prostatic hyperplasia. This reference attests to the fact that both the effects of estrogen and the effects of androgen are important since medicaments directed against each are necessary. The method of this patent is disadvantageous since the physiological effect of the antiestrogens is highly dosage specific; for example, at relatively high doses, antiestrogens will act agonistically, i.e., as estrogens. Similarly, the mentioned treatment of U.S. Pat. No. 3,423,507 using gestagenically and antiandrogenically active esters such as cryproterone esters, is disadvantageous since only a partial regression of the hyperplasia is effected, no doubt due to the failure to treat the estrogenic factors. All of the evidence shows that both factors must be treated.

A further suggestion of the role of increased estrogen levels in the development of BPH is contained in the disclosures of H. U. Schweikert (1979): "Conversion of androstenedione to estrone in human fibroblasts cultured from prostate, genital and nongenital skin." Horm. Metab. Res. 11, 635-640; Schweikert, H. U., Hein, H. J. and F. H. Schroeder: "Androgen metabolism in fibroblasts from human benign prostatic hyperplasia, prostatic carcinoma and nongenital skin" 'Steroid receptors, metabolism and prostatic cancer.' Editors: F. H. Schroeder and H. J. de Voogt, pages 126-133, Excerpta Medica (1980), International Congress Series No. 494, Amsterdam, Oxford, Princeton. These references report the results of studies showing that fibroblast cultures from human prostatic hyperplasia tissue are able to aromatize testosterone to form the corresponding estrogens more strongly than fibroblast cultures originating from healthy prostate tissue. The phenomenon of aromatization of androgens to form estrogens in the prostate gland is consistent with previous findings that estrogens present in men originate predominantly from peripheral aromatization of androgenic hormones and not from testicular biosynthesis, as contained in the disclosures of H. U. Schweikert: "Befunde zum Androgenmetabolismus" in 'Androgenisierungserscheinungen bei der Frau,' editors: J. Hammerstein, U. Lachnit-Fixson, F. Neumann and G. Plewig, pages 42-50, Excerpta Medica (1979), Amsterdam, Oxford, Princeton; MacDonald, P. C., Rombaut, R. P. and P. K. Siiteri (1967); "Plasma precursors of estrogen. I. Extent of conversion of plasma $\Delta^4$-androstenedione to estrone in normal males and nonpregnant normal, castrate and adrenalectomized females." J. Clin. Endocrinol. Metab. 27, 1103-1111; Weinstein, R. L., Kelch, R. P., Jenner, M. R., Kaplan, S. L. and M. M. Grumbach (1974): "Secretion of unconjugated androgens and estrogens by the normal and abnormal testis before and after human chorionic gonadotropin." J. Clin. Invest. 53, 1–6.

It can thus be seen that BPH is a condition considered by the prior art to be caused both by increased estrogen levels and increased androgen levels or an increase in the estrogen/androgen ratio. The precise etiology has not yet been elucidated. Because of the existence of both estrogenic and androgenic factors, proposed hormonal treatments have been less than satisfactory and have not been predictable with any degree of reliability. For example, if one were to consider the possibility of inhibiting the aromitization of androgens into estrogens using any of the known aromatase-inhibitors, it could not be expected that such treatment would be successful. As indicated, an increase in the amount of androgens has been established as one cause of BPH. Since an aromatase-inhibitor would decrease the amount of estrogen, but at the same time would increase the relative amount of androgen, offsetting effects must be expected. In fact, studies involving a known aromatase-inhibitor confirm such offsetting effects. In these studies, it has been shown that the known aromatase-inhibitor, $\Delta^1$-testolactone (Teslac ®), does inhibit the conversion of androgens to estrogens, thereby causing a fall in the serum estrogen level; however, at the same time, it causes a rise in the serum androgen level. (See, e.g., R. A. Vigersky and A. R. Glass, "Effects of $\Delta^1$-Testolactone on the Pituitary-Testicular Axis in Oligospermic Men," J. Clin. Endocrin. and Metab., 52, 897–902 (1981); R. M. Barone, I. M. Shamonki, P. K. Siiteri, and H. L. Judd, "Inhibition of Peripheral Aromatization of Androstenedione to Estrone in Postmenopausal Women with Breast Cancer Using $\Delta^1$-Testolactone," J. Clin. Endocrin. and Metab., 49, 672–676 (1979); S. P. Marynick, D. L. Loriaux, R. J. Sherins, J. C. Pita, Jr., and M. B. Lipsett, "Evidence That Testosterone Can Suppress Pituitary Gonadotropin Secretion Independently of Peripheral Aromatization," J. Clin. Endocrin. and Metab., 49, 396–398 (1979); and P. K. Siiteri and E. Aubrey Thompson, "Studies of Human Placental Aromatase," J. Ster. Biochem., 6, 317–332 [1975].) Thus, administration of an aromatase-inhibitor (e.g., also including the aromatase-inhibitors disclosed in U.S. Pat. No. 4,235,893), would be expected to have a beneficial effect on BPH in view of the fact that it would lower estrogen levels; however, in view of the fact that its administration would be expected to increase androgen levels, it would be expected to have a negative influence on BPH. Accordingly, the prior art contains no suggestion that administration of an aromatase-inhibitor could be effective in treating BPH. Their use in the prior art has been restricted to indications involving increased estrogen levels only, and not increased androgen levels. (U.S. Pat. No. 4,235,893.)

Since the prostate gland of men possesses estrogen receptors and the interstice (stroma) is a target organ for estrogens in BPH, the estrogens bring about the stimulation of the fibromuscular tissue. From this it follows that, in humans, prostatic hyperplasia stimulated by estrogens is predominantly a disorder of the fibromuscular interstice (stroma).

These findings are also supported by investigations carried out on dogs. It has been possible to show that estrogen treatment leads to a stimulation of the glandular epithelium (parenchyma) (Tunn, U. W., Schuering, B., Senge, Th., Neumann, F., Schweikert, H. U. and H. P. Rohr (1981): "Morphometric analysis of prostates in castrated dogs after treatment with androstanediol, estradiol and cyproterone acetate," Invest. Urol. 18: 289–292). These studies also clearly show that both estrogenic effects and androgenic effects are important in BPH. Also, in autoradiographic studies on human prostatic hyperplasia tissue, it has been possible to show that it is only the glandular epithelium (parenchyma) that is a target organ for androgens, and not the interstice.

SUMMARY OF THE INVENTION

Accordingly, it is an object of this invention to provide an agent and method for treatment or prophylaxis of BPH in men.

Upon further study of the specification and appended claims, further objects and advantages of this invention will become apparent to those skilled in the art.

These objects have been achieved according to the present invention by preventing the formation of biologically active estrogens by administering aromatase-inhibitors. The stimulation of the fibromuscular tissue is thereby prevented and, despite any increase in androgen level which might accompany the administration, regression results accompanied by a decrease in size. This brings about the desired improvement in the clinical symptoms (e.g., micturition discomfort).

The present invention relates to aromatase-inhibitors for use in a method of prophylaxis of benign prostatic hyperplasia and/or of treatment by therapy of benign prostatic hyperplasia and, particularly, to a method for the treatment of benign prostatic hyperplasia in a male human patient suffering therefrom comprising administering to the patient an amount of aromatase-inhibitor effective to treat benign prostatic hyperplasia, or, to a method for the prophylaxis of benign prostatic hyperplasia in a male human patient not suffering from benign prostatic hyperplasia but in whom prophylactic treatment against benign prostatic hyperplasia is desired, comprising administering an amount of an aromatase-inhibitor effective to prevent benign prostatic hyperplasia.

DETAILED DISCUSSION

Suitable for use according to the present invention are all substances that act as aromatase-inhibitors, i.e., those which act as a substrate for an aromatase. They themselves must not possess estrogenic or other hormonal actions in addition to their action on the aromatization. Also, the products of the aromatization produced from them must also possess essentially no estrogenic or other hormonal actions.

Suitable such aromatase-inhibitors include testolactone (17a-oxa-D-homoandrosta-1,4-diene-3,17-dione); there may also be mentioned as the aromatase-inhibitor, for example, the following known compounds:
androsta-4,6-diene-3,17-dione,
androsta-4,6-dien-17$\beta$-ol-3-one acetate,
androsta-1,4,6-triene-3,17-dione,
androst-4-ene-19-chloro-3,17-dione,
androst-4-en-17$\beta$-ol-3-one acetate,
androst-4-en-17$\beta$-ol-3-one formate,
androst-4-en-17$\beta$-ol-3-one propionate and
androst-4-ene-3,6,17-trione, and also
androst-4-en-4-ol-3,17-dione and esters thereof,
for example the acetate, heptanoate, dodecanoate, hemisuccinate and benzoate and others disclosed in Endo. 92 (1973) 866–880 and U.S. Pat. No. 4,235,893, e.g., generally, the $C_{2-12}$-alkanoates, whose disclosure is incorporated by reference herein.

Of course, the aromatase itself, of which the compound to be administered by this invention must be an inhibitor, is any aromatase found in the human male which effects aromatization of a compound to form an estrogenic substance.

To demonstrate the efficacy of the method of this invention, the following tests were performed:

In patients with decompensated benign prostatic hyperplasia (state III), spontaneous micturition is no longer possible (urine retention). These patients are given a suprapubic vesical fistula catheter by means of suprepubic vesical paracentesis under local anaesthesia. The vesical fistula catheter therefore has two functions:
1. If urine retention continues, the bladder is emptied via the catheter; when the urinary bladder is full, the patient can open and close the fistula catheter by himself.
2. The functional effectiveness of an initiated therapy is indicated by the fact that the patient can again urinate spontaneously, since the vesical fistula catheter does not interfere with spontaneous micturition. At the same time the patient can, on-occurrence of spontaneous micturition, check the residual amounts of urine after each micturition by means of the vesical fistula catheter.

The results of a testolactone treatment (200 mg per os daily) of 10 patients having benign prostatic hyperplasia (stage III) are summarized in Table 1 below.

TABLE 1

Results of a testolactone treatment with 200 mg daily per os in the case of patients having benign prostate hyperplasia, stage III (a) Spontaneous micturition and size of prostate gland

| serial no. | initials | age | duration of therapy (months) until spontaneous micturition | size of the prostate gland in grams initial | after 8 months |
|---|---|---|---|---|---|
| 1 | J.O. | 81 | 3 | 40 | 10 |
| 2 | W.W. | 77 | 4 | 80 | 20 |
| 3 | G.L. | 79 | 2 | 40 | 25 |
| 4 | D.S. | 81 | 4 | 70 | 25 |
| 5 | W.S. | 79 | 2 | 50 | 40 |
| 6 | F.B. | 69 | 5 | 50 | 40 |
| 7 | H.M. | 61 | 2 | 40 | 25 |
| 8 | K.H. | 73 | 4 | 40 | 20 |
| 9 | E.N. | 59 | 3 | 50 | 20 |
| 10 | K.G. | 75 | 4 | 60 | 30 |
| x̄ | | 73.40 | 3.30 | 52.00* | 25.50* |
| S.D. | | 7.99 | 1.06 | 13.98 | 9.26 |

(b) Uroflow-measurement

| serial no. | initials | age | uroflow parameters (after 8 months) | | | |
|---|---|---|---|---|---|---|
| | | | residual urine (ml) | max. flow (ml/sec.) | t (sec.) | mict. vol. (ml) |
| 1 | J.O. | 81 | 0 | 10 | 21 | 150 |
| 2 | W.W. | 77 | 0 | 11 | 60 | 300 |
| 3 | G.L. | 79 | 0 | 13 | 32 | 190 |
| 4 | D.S. | 81 | 0 | 21 | 40 | 300 |
| 5 | W.S. | 79 | 20 | 9 | 33 | 200 |
| 6 | F.B. | 69 | 50 | 6 | 60 | 180 |
| 7 | H.M. | 61 | 0 | 16 | 78 | 540 |
| 8 | K.H. | 73 | 20 | 13 | 62 | 480 |
| 9 | E.N. | 59 | 0 | 25 | 15 | 210 |
| 10 | K.G. | 75 | 0 | 14 | 65 | 450 |
| x̄ | | 73.40 | | 13.80 | 46.60 | 300.00 |
| S.D. | | 7.99 | | 5.67 | 21.13 | 141.26 |

*$p < 0.001$

In the case of the 10 patients studied, the average duration of therapy until the commencement of spontaneous micturition was 3.3 months ($\pm 1.1$ months). After 8 months' therapy, 7 out of 10 patients were able to urinate without leaving residual urine. In the case of two patients the residual urine was 20 ml in each case and in the case of one patient it was 50 ml. The urine flow parameters measured by a uroflowmeter gave on average a maximum flow rate of 13.8 ml/sec. (limit value: 6 to 25 ml/sec.) with an average micturition time of 46.6 seconds and an average micturition volume of 300 ml (See Table 1b).

The size of the prostate gland estimated by digito-/rectal examination indicated a reduction in the size of the prostate gland of, on average, approximately one half after 8 months' therapy. This should be qualified by mentioning that the subjective estimation of the volume of the prostate gland, even with great experience, is to be regarded only as a relative parameter.

The daily dose for male human beings of the aromatase-inhibitor when used in accordance with the present invention is 10 mg to 400 mg, preferably 50 mg to 250 mg, of testolactone (17a-oxa-D-homo-androsta-1,4-diene-3,17-dione) or a biologically equivalent amount of another aromatase-inhibitor. Another aromatase-inhibitor may be a single aromatase-inhibitor or a combination of 2 or more aromatase-inhibitors, one of which may, if desired, be testolactone. Biologically equivalent amounts of aromatase-inhibitors can be determined using any conventional protocol or procedure permitting a determination of the aromatization inhibition achieved by a compound such as those procedures described in the foregoing references relating to aromatase-inhibitors and their effects. A particularly preferred such practice is disclosed in Brueggemeier et al, J. of Med. Chem., 1978, Vol 21, No. 10, p. 1007, whose disclosure is incorporated by reference herein. That is, equivalent amounts can be determined using fully conventional procedures employed in differential potency determinations.

The aromatase-inhibitor is preferably administered orally, but may also be administered parenterally, especially intramuscularly, one or more times daily with proportionately smaller multiple doses. The same administration characteristics also apply to the use of the pharmaceutical preparation of this invention in the prophylaxis of BPH. Such administration will be dictated for a given patient as usual where a doctor has conventionally determined that the patient has an abnormally high risk of developing BPH, e.g., where the patient has a family history of BPH or where the patient has reached an advanced age. The onset of prophylactic administration in the adult human male will usually be in the range of 50–65 years.

The administration of any aromatase-inhibitor of this invention in the method of this invention will be fully analogous to the administration of testalactone for the same purpose, e.g., as described in the tests reported above.

The present invention also provides a pharmaceutical preparation suitable for use according to the present invention, which comprises an aromatase-inhibitor in admixture or conjunction with a pharmaceutically suitable carrier. The preparation may be in any conventional form suitable for oral or parenteral administration and/or may be in unit dosage form.

The aromatase-inhibitors used in accordance with the present invention may be processed by methods known per se into the usual forms of administration together with, for example, the additives, carrier substances and/or taste correctives customarily used in galenical pharmacy.

For the preferred oral administation there are usually used, more especially, tablets, dragees, capsules, pills, suspensions or solutions. For parenteral, especially intramuscular, administration, oily solutions are suitable, for example sesame oil or castor oil solutions. Solubilizers, for example benzyl benzoate or benzyl alcohol, may be added to increase solubility. The oily solutions may, if desired, be stored in ampules.

The pharmacologically active compounds of this invention can be processed in accordance with conventional methods of galenic pharmacy to produce medicinal agents for administration to humans. Conventional excipients are pharmaceutically acceptable organic or inorganic carrier substances suitable for parenteral or enteral application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, ampules are convenient unit dosages.

For enteral application, particularly suitable are tablets, dragees, suppositories, or capsules having talc and/or a carbohydrate carrier or binder or the like, the carrier preferably being lactose and/or corn starch and/or potato starch. A syrup, elixier or the like can be used wherein a sweetened vehicle is employed. Dosages for a given host can be determined using conventional considerations, e.g., by customary comparison of the differential activities of the subject compound and of another agent, e.g., testolactone by means of an appropriate, conventional pharmacological protocol. Administration in accordance with this invention is conventional except where indicated otherwise herein.

For use according to the present invention, the aromatase-inhibitor may be in the form of a unit dosage preparation containing in each dosage unit the daily amount of the aromatase-inhibitor required for the method of prophylaxis and/or of treatment by therapy of prostatic hyperplasia.

The unit dosage preparations formulated as indicated above contain per dosage unit, when in a form suitable for oral administration, preferably from 10 mg to 250 mg and, when in a form suitable for parenteral administration, preferably from 20 mg to 200 mg of testolactone, or the biologically equivalent amount in each case of another aromatase-inhibitor.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

| Composition of a tablet | |
|---|---|
| 20.0 mg | of 17a-oxa-D-homo-androsta-1,4-diene-3,17-dione (testolactone) |
| 130.5 mg | of lactose |
| 69.5 mg | of maize starch |
| 2.5 mg | of poly-N—vinylpyrrolidone 25 |
| 2.0 mg | of Aerosil |
| 0.5 mg | of magnesium stearate |
| 225.0 mg | total weight of the tablet, which was manufactured in the usual manner on a tablet press |

EXAMPLE 2

| Composition of a tablet | |
|---|---|
| 50.0 mg | of 17a-oxa-D-homo-androsta-1,4-diene-3,17-dione (testolactone) |
| 115.5 mg | of lactose |
| 54.5 mg | of maize starch |
| 2.5 mg | of poly-N—vinylpyrrolidone 25 |
| 2.0 mg | of Aerosil |
| 0.5 mg | of magnesium stearate |
| 225.0 mg | total weight of the tablet, which was manufactured in the usual manner on a tablet press |

EXAMPLE 3

| Composition of an oily solution | |
|---|---|
| 50.0 mg | of 17a-oxa-D-homo-androsta-1,4-diene-3,17-dione (testolactone) |
| 378.4 mg | of castor oil |
| 643.6 mg | of benzyl benzoate |
| 1072.0 mg | $\triangleq$ 1 ml solution |

The solution was introduced into an ampule and sterilized.

EXAMPLES 4–31

Examples 2 and 3 are repeated except that, instead of testolactone, this is substituted in each respective tablet or oily solution:
50.0 mg of:
androsta-4,6-diene-3,17-dione,
androsta-4,6-dien-17β-ol-3-one acetate,
androsta-1,4,6-triene-3,17-dione,
androst-4-ene-19-chloro-3,17-dione,
androst-4-en-17β-ol-3-one acetate,
androst-4-en-17β-ol-3-one formate,
androst-4-en-17β-ol-3-one propionate and
androst-4-ene-3,6,17-trione, as well as
androst-4-en-4-ol-3,17-dione and the acetate, heptanoate, dodecanoate, hemisuccinate and benzoate esters thereof.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for the treatment of benign prostatic hyperplasia in a male human patient suffering therefrom comprising, administering to the patient an amount of an aromatase-inhibitor effective to treat benign prostatic hyperplasia; wherein the aromatase inhibitor possesses essentially no hormonal effects and products of the aromatization therewith in the patient possess essentially no hormonal effects.

2. A method for the prophylaxis of benign prostatic hyperplasia in a male human patient not suffering from benign prostatic hyperplasia but in whom prophylactic treatment against benign prostatic hyperplasia is desired, comprising, administering to the patient an amount of an aromatase-inhibitor effective to prevent benign prostatic hyperplasia; wherein the aromatase inhibitor possesses essentially no hormonal effects and products of the aromatization therewith in the patient possess essentially no hormonal effects.

3. A method of claim 1 or 2 wherein the aromatase-inhibitor is testolactone.

4. A method of claim 1 or 2 wherein the aromatase-inhibitor is androsta-4,6-diene-3,17-dione, androsta-4,6-dien-17β-ol-3-one acetate, androsta-1,4,6-triene-3,17-dione, androst-4-ene-19-chloro-3,17-dione, or androst-4-ene-3,6,17-trione.

5. A method of claim 1 or 2 wherein the aromatase-inhibitor is androst-4-en-4-ol-3,17-dione or a 4-ester thereof.

6. A method of claim 5 wherein the aromatase-inhibitor is androst-4-en-4-ol-3,17-dione.

7. A method of claim 5 wherein the aromatase-inhibitor is the $C_{2-12}$-alkanoate, hemisuccinate or benzoate ester.

8. A method of claim 7 wherein the ester is the acetate, heptanoate, dodecanoate, hemisuccinate or benzoate.

9. A method of claim 1 or 2 wherein the amount of aromatase-inhibitor administered daily is 10 mg to 400 mg of testolactone or a biologically equivalent amount of another aromatase-inhibitor.

10. A method of claim 9 wherein the amount of aromatase-inhibitor administered daily is 50 mg to 250 mg of testolactone or a biologically equivalent amount of another aromatase-inhibitor.

11. A method of claim 1 or 2 wherein the aromatase-inhibitor is administered orally.

12. A method of claim 2 wherein the adult human has a family history of benign prostatic hypertrophy and is of an age of about 50 years or older.

13. A method of claim 1, wherein the aromatase inhibitor is not androst-4-ene-19-(al or ol)-3,17-dione.

14. A method of claim 2, wherein the aromatase inhibitor is not androst-4-ene-19-(al or ol)-3,17-dione.

15. A method of claim 1, wherein the compound administered as said aromatase inhibitor was not per se previously administered for the treatment of benign prostatic hyperplasia.

16. A method of claim 2, wherein the compound administered as said aromatase inhibitor was not per se previously administered for the treatment of benign prostatic hyperplasia.

17. A method of claim 1, wherein the compound administered as said aromatase inhibitor was evaluated to determine its aromatase inhibition efficacy and on the basis of the resultant determined efficacy was selected as said aromatase inhibitor to be used in said method.

18. A method of claim 2, wherein the compound administered as said aromatase inhibitor was evaluated to determine its aromatase inhibition efficacy and on the basis of the resultant determined efficacy was selected as said aromatase inhibitor to be used in said method.

19. A method of claim 1, wherein the compound administered as said aromatase inhibitor was previously known to treat benign prostatic hypertrophy but not as an aromatase inhibitor, and the compound was tested to determine its aromatase inhibition efficacy prior to administration in said method.

20. A method of claim 2, wherein the compound administered as said aromatase inhibitor was previously known for the prophylaxis of benign prostatic hypertrophy but not as an aromatase inhibitor, and the compound was tested to determine its aromatase inhibition efficacy prior to administration in said method.

21. A method of claim 1, further comprising, prior to said administering, evaluating the aromatase inhibitor compound to determine its aromatase inhibition efficacy and on the basis of the resultant determined efficacy, selecting said compound as the aromatase inhibitor in said method.

22. A method of claim 2, further comprising, prior to said administering, evaluating the aromatase inhibitor compound to determine its aromatase inhibition efficacy and on the basis of the resultant determined efficacy, selecting said compound as the aromatase inhibitor in said method.

23. A method of claim 1, wherein the compound administered as said aromatase inhibitor was previously known to treat benign prostatic hypertrophy but not as an aromatase inhibitor, and further comprising, prior to said administering, testing the compound to determine its aromatase inhibition efficacy.

24. A method of claim 1, wherein the compound administered as said aromatase inhibitor was previously known for the prophylaxis of benign prostatic hypertrophy but not as an aromatase inhibitor, and further comprising, prior to said administering, testing the compound to determine its aromatase inhibition efficacy.

25. A method for the treatment of benign prostatic hyperplasia in a male human patient suffering therefrom comprising, administering to the patient an amount of an aromatase inhibitor effective to treat benign prostatic hyperplasia, wherein the aromatase inhibitor possesses essentially no estrogenic effects and products of the aromatization therewith in the patient possess essentially no estrogenic effects.

26. A method for the prophylaxis of benign prostatic hyperplasia in a male human patient not suffering from benign prostatic hyperplasia but in whom prophylactic treatment against benign prostatic hyperplasia is desired, comprising, administering to the patient an amount of an aromatase-inhibitor effective to prevent benign prostatic hyperplasia; wherein the aromatase inhibitor possesses essentially no estrogenic effects and products of the aromatization therewith in the patient possess essentially no estrogenic effects.

27. A method of claim 25 wherein the aromatase inhibitor also has essentially no androgenic effects and products of the aromatization therewith in the patient possess essentially no androgenic effects.

28. A method of claim 26 wherein the aromatase inhibitor also has essentially no androgenic effects and products of the aromatization therewith in the patient possess essentially no androgenic effects.

29. A method for the treatment of benign prostatic hyperplasia in a male human patient suffering therefrom comprising, administering to the patient an amount of an aromatase inhibitor effective to treat benign prostatic hyperplasia; wherein the aromatase inhibitor possesses an estrogenic effect lower than that of natural estrogen in the patient and products of the aromatization therewith in the patient possess estrogenic effects lower than that of natural estrogen in the patient.

30. A method for the prophylaxis of benign prostatic hyperplasia in a male human patient not suffering from benign prostatic hyperplasia but in whom prophylactic treatment against benign prostatic hyperplasia is desired, comprising, administering to the patient an amount of an aromatase-inhibitor effective to prevent benign prostatic hyperplasia; wherein the aromatase inhibitor possesses an estrogenic effect lower than that of natural estrogen in the patient and products of the aromatization therewith in the patient possess estrogenic effects lower than that of natural estrogen in the patient.

31. A method of claim 29 wherein the aromatase inhibitor also has an androgenic effect lower than that of natural androgen in the patient and products of the aromatization therewith in the patient prossess androgenic effects lower than that of natural androgen in the patient.

32. A method of claim 30 wherein the aromatase inhibitor also has an androgenic effect lower than that of natural androgen in the patient and products of the aromatization therewith in the patient prossess androgenic effects lower than that of natural androgen in the patient.

* * * * *